United States Patent
Qureshi et al.

(10) Patent No.: US 7,318,815 B2
(45) Date of Patent: Jan. 15, 2008

(54) ANGIOPLASTY DEVICE WITH EMBOLIC RECAPTURE MECHANISM FOR TREATMENT OF OCCLUSIVE VASCULAR DISEASES

(76) Inventors: Adnan I. Qureshi, 58 Tillinghast Pl., Buffalo, NY (US) 14216; Afshin A. Divani, 240 Niagara Falls Blvd., #1N, Buffalo, NY (US) 14223

(*) Notice: Subject to any disclaimer, the term of this patent is extended or adjusted under 35 U.S.C. 154(b) by 737 days.

(21) Appl. No.: 10/187,929

(22) Filed: Jul. 2, 2002

(65) Prior Publication Data
US 2004/0006307 A1    Jan. 8, 2004

(51) Int. Cl.
*A61M 25/00* (2006.01)
(52) U.S. Cl. .................... 604/96; 606/194
(58) Field of Classification Search ............ 604/99.02, 604/103.01, 104, 194, 509, 96, 97, 102, 264; 606/110, 113, 114, 159, 194, 200
See application file for complete search history.

(56) References Cited

U.S. PATENT DOCUMENTS

| 3,834,394 | A | | 9/1974 | Hunter et al. |
|---|---|---|---|---|
| 5,320,634 | A | | 6/1994 | Vigil et al. |
| 5,342,307 | A | | 8/1994 | Euteneuer et al. |
| 5,350,361 | A | | 9/1994 | Tsukashima et al. |
| 5,395,311 | A | * | 3/1995 | Andrews ............ 604/22 |
| 5,458,575 | A | | 10/1995 | Wang |
| 5,649,941 | A | * | 7/1997 | Lary .................. 606/159 |
| 5,704,913 | A | * | 1/1998 | Abele et al. ....... 604/101.02 |
| 5,954,741 | A | | 9/1999 | Fox |
| 6,231,588 | B1 | * | 5/2001 | Zadno-Azizi ......... 606/200 |
| 6,264,672 | B1 | | 7/2001 | Fisher |
| 6,290,710 | B1 | | 9/2001 | Cryer et al. |
| 6,443,926 | B1 | * | 9/2002 | Kletschka ........... 604/96.01 |

* cited by examiner

*Primary Examiner*—Michael J. Hayes
*Assistant Examiner*—Victor Nguyen
(74) *Attorney, Agent, or Firm*—Hodgson Russ LLP

(57) ABSTRACT

An angioplasty device with emboli pull-in mechanism is provided that includes an infusion catheter with a proximal end and a distal end. A balloon catheter having an inflatable cavity formed by an inner wall and an outer wall is disposed coaxially with the infusion catheter. The balloon catheter has a proximal end and a distal end. The distal end of the balloon catheter is sealingly attached to the infusion catheter. And the balloon catheter has at least one communicating channel disposed from the outer wall to the inner wall of the balloon catheter. A suction catheter is disposed between the balloon catheter and the infusion catheter. The suction catheter is in fluid communication with the at least one communicating channel in the balloon catheter.

11 Claims, 10 Drawing Sheets

ANGIOPLASTY DEVICE WITH EMBOLIC RECAPTURE MECHANISM FOR TREATMENT OF OCCLUSIVE VASCULAR DISEASES

FIELD OF INVENTION

The present invention relates to a medical device suitable for use in intravascular angioplasty.

BACKGROUND OF THE INVENTION

Release of atherosclerotic debris is the primary cause of ischemic events such as stroke or myocardial infarction during a routine intravascular angioplasty. A standard balloon inflates and deflates via the change in pressure induced by contrast material and saline. The balloon provides a radial force to the surrounding vessel wall resulting in dilation of occlusive lesions in the vessel wall. The process nevertheless releases debris from the site of angioplasty that can migrate distally with the blood flow to occlude small blood vessels resulting in catastrophic outcomes. While the balloon is completely inflated, the loosened plaque particles are compressed against the vessel wall. However, once the balloon is deflated, the plaque particles can move freely with the blood stream into the distal vasculature and embolize arteries of various sizes. Plaque particles of 100 micron or larger can occlude small and medium size vessels. Conventional angioplasty balloons cannot provide protection against debris generated during an angioplasty procedure. In recent years, the use of an embolic protection device is suggested to capture embolic debris during angioplasty. Distal protection devices, such as filters, are under investigation to be placed distal to site of occlusion to block the passage of particles. Different devices are introduced to the market with various degrees of success in capturing plaque particles. However, the use of new embolic protection devices requires insertion and position of the device into the artery distal to the angioplasty site. In many cases the lumen of the artery at the atherosclerotic site is reduced to a point that passage of any extra device is difficult. Furthermore, tortuosity and angulation of the distal vessels prevent successful placement of protection devices. What is needed is a balloon that can perform angioplasty and at the same time prevent the release of embolic debris.

SUMMARY OF THE INVENTION

The present invention meets the above-described need by providing an angioplasty device having a balloon catheter with an embolic recapture mechanism that does not require deployment of a trap located beyond the balloon catheter in the distal direction.

The present invention provides an angioplasty catheter having an infusion catheter with a proximal end and a distal end. A balloon catheter having an inflatable cavity formed by an inner wall and an outer wall is disposed coaxially with the infusion catheter. The balloon catheter has a proximal end and a distal end. The distal end of the balloon catheter is sealingly attached to the infusion catheter. And the balloon catheter has at least one communicating channel disposed from the outer wall to the inner wall of the balloon catheter. A suction catheter is disposed between the balloon catheter and the infusion catheter. The suction catheter is in fluid communication with the at least one communicating channel in the balloon catheter.

BRIEF DESCRIPTION OF THE DRAWINGS

The invention is illustrated in the drawings in which like reference characters designate the same or similar parts throughout the figures of which.

DETAILED DESCRIPTION

Figure 1:
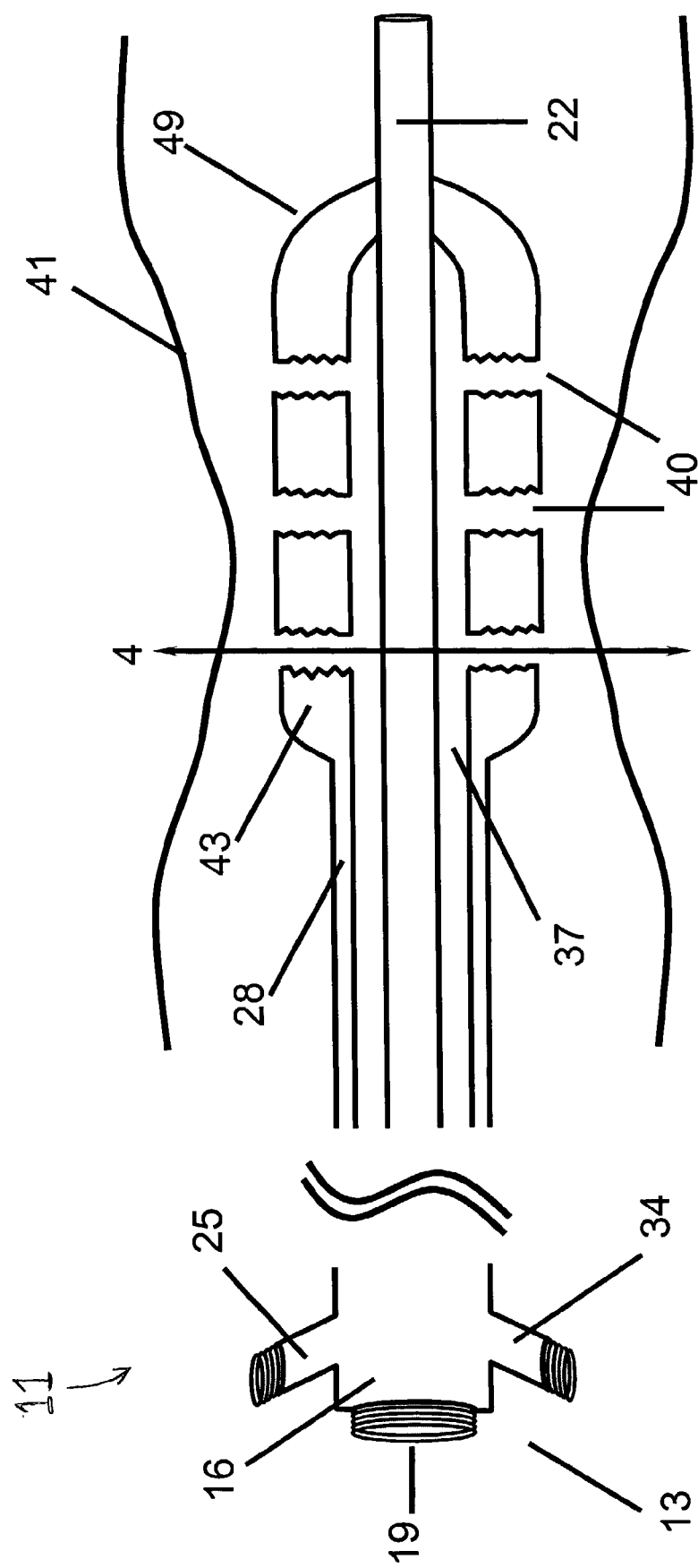
FIG. 1 is a side view of the balloon catheter of the present invention in the deflated state.
Figure 2:
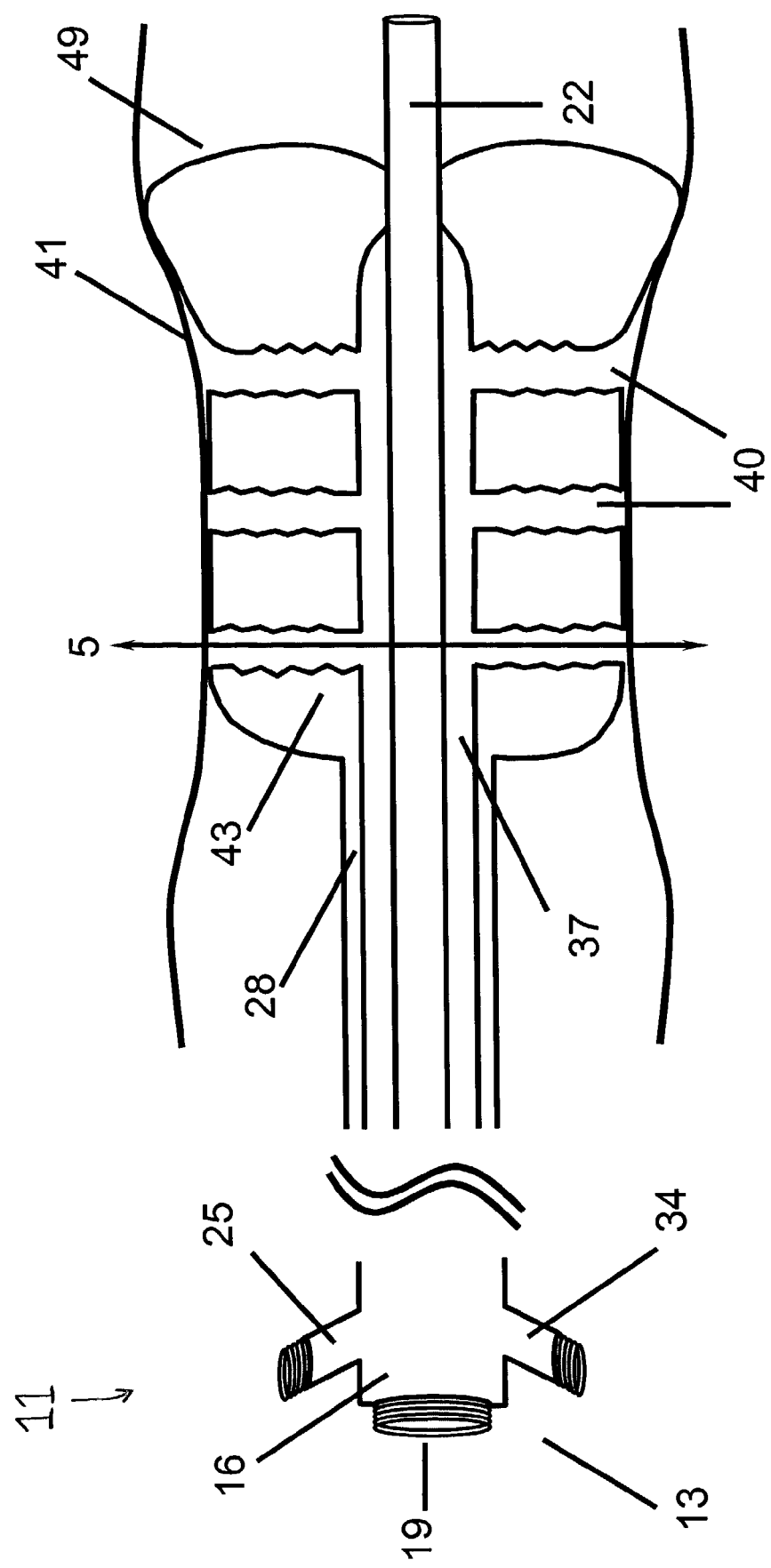
FIG. 2 is a side view of the balloon catheter of FIG. 1 in the completely inflated state.
Figure 3:
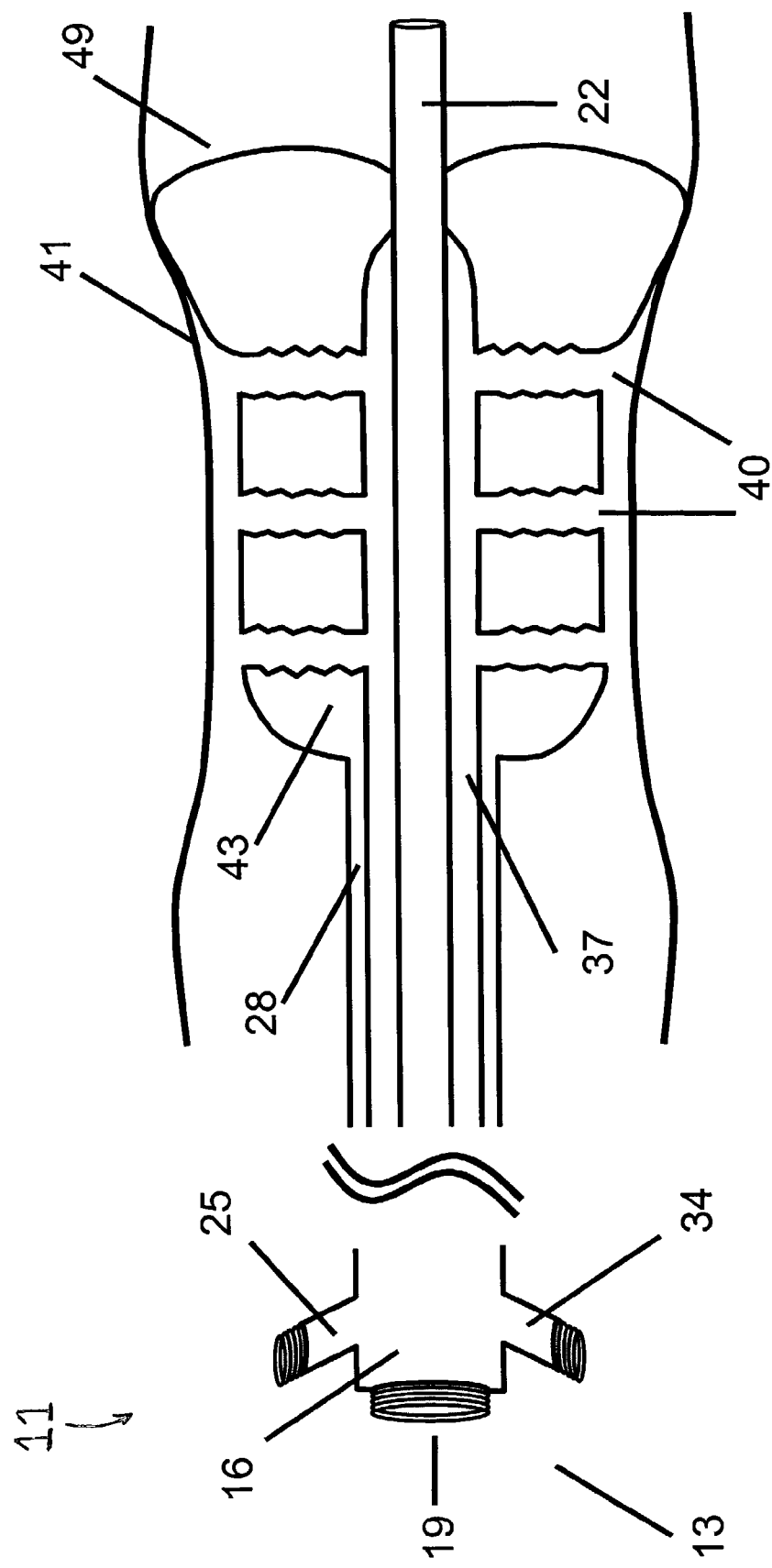
FIG. 3 is a side view of the balloon catheter of FIG. 1 in a partially deflated state.

Referring to FIGS. 1-5 generally and initially to FIG. 1, the present invention comprises an angioplasty device 11 having a suction mechanism for the removal of plaque particles. The device 11 includes an assembly having three co-axial catheters. The proximal end 13 of the assembly is connected to a three-way connector 16. The center port 19 of the connector 16 is coupled to an infusion catheter 22 which is the most inner catheter. A first side-branch 25 of the connector 16 is connected to a balloon catheter 28 which is the outermost catheter. The first side-branch 25 is used for inflating and deflating the balloon 43. A second side-branch 34 is connected to a suction catheter 37 which is located in the middle between the other catheters. The balloon catheter 28 is furnished with multiple communicating channels 40 that act as tunnels between the suction catheter 37 and blood stream. Upon enlargement of the lumen 41 by balloon 43 at the atherosclerotic site, suction of the debris is performed through the communicating channels 40 using a standard syringe (not shown) that is connected to the corresponding port of the three-way connector 16. The diameters of communicating channels 40 are adjusted for the maximum size of the atherosclerotic particles. Their lengths are determined based on the radius of the balloon 43 in its expanded position. The communicating channels 40 can be made of elastic material that will be elongated during the expansion of the balloon. Another design of communicating channels 40 comprises an accordion pleat shape. This design enables the communicating channels to be elongated without exerting any strain on the surface of the balloon 43. The communicating channels 40 can also be made out of fibrous material for reinforcement of its structure to reduce its collapsibility during expansion of the balloon 43 or suction process. The position of the communicating channels 40 is adjusted in both the longitudinal and the radial direction on the balloon 43 to maximize performance of the device. The balloon 43 is made of asymmetric material with the distal portion 49 to be thinner such that it allows larger expansion of the balloon 43. This larger expansion can restrain the atherosclerotic particles upstream of the balloon portion of the device during deflation phase and ensures all of the particles to be suctioned out into the catheter 28 and not travel with the blood stream. The deflation of the balloon 43 because of its design would be stepwise. The distal part 49 of the balloon 43 would deflate last to avoid escape of debris particles distal to the site of angioplasty.

In operation, the device 11 of the present invention is deployed by means of an introducer sheath(s) having a low profile. As known to those of ordinary skill in the art, the device 11 is deployed over a guide wire (not shown) to the target area of the vasculature. Once the device reaches the target area, the balloon 43 is inflated by injecting contrast material and saline into the cavity formed inside the balloon 43. The inflation of the balloon 43 from the state shown in FIG. 1 to the state shown in FIG. 2 causes the balloon 43 to expand such that it engages with the inner wall of the lumen 41.

Figure 4:
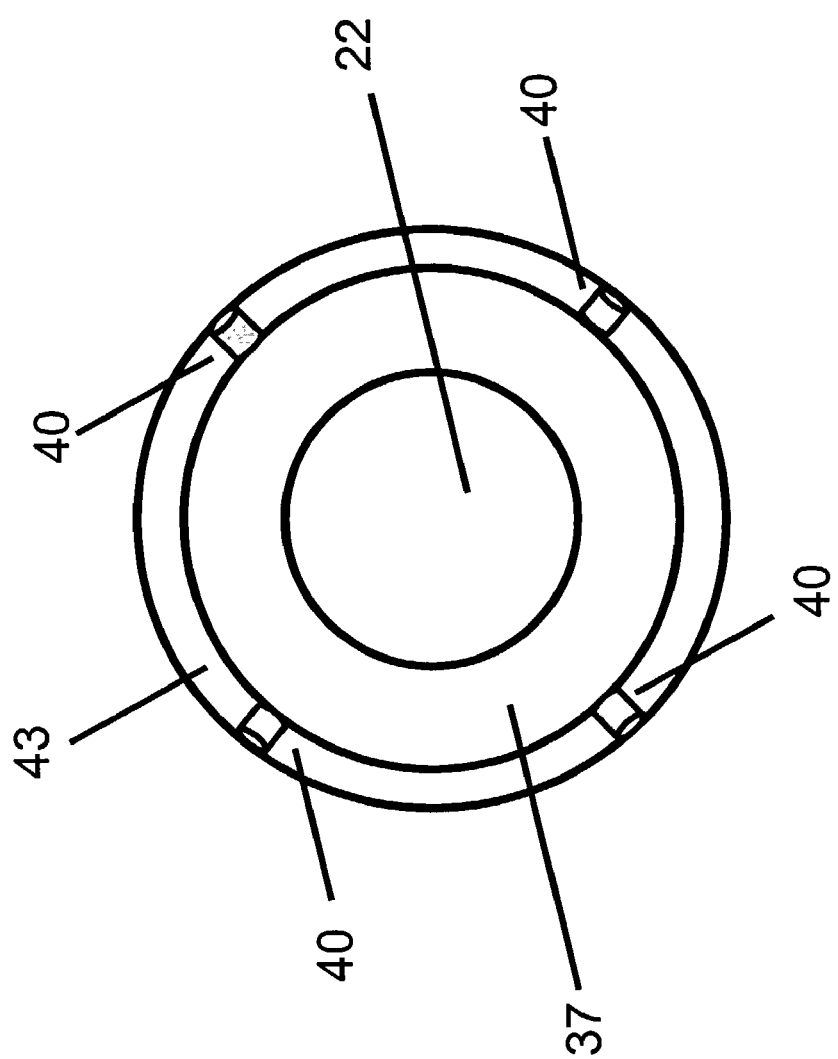
FIG. 4 is a cross-sectional view taken along line 4-4 of FIG. 1.

In FIG. 4, the balloon 43 is shown in its deflated state with the co-axial infusion catheter 22, suction catheter 37, and balloon 43. The communicating channels 40 are formed in the walls of the balloon 43 such that particles can be suctioned from the vessel lumen through the balloon into the suction catheter 37.

Figure 5:
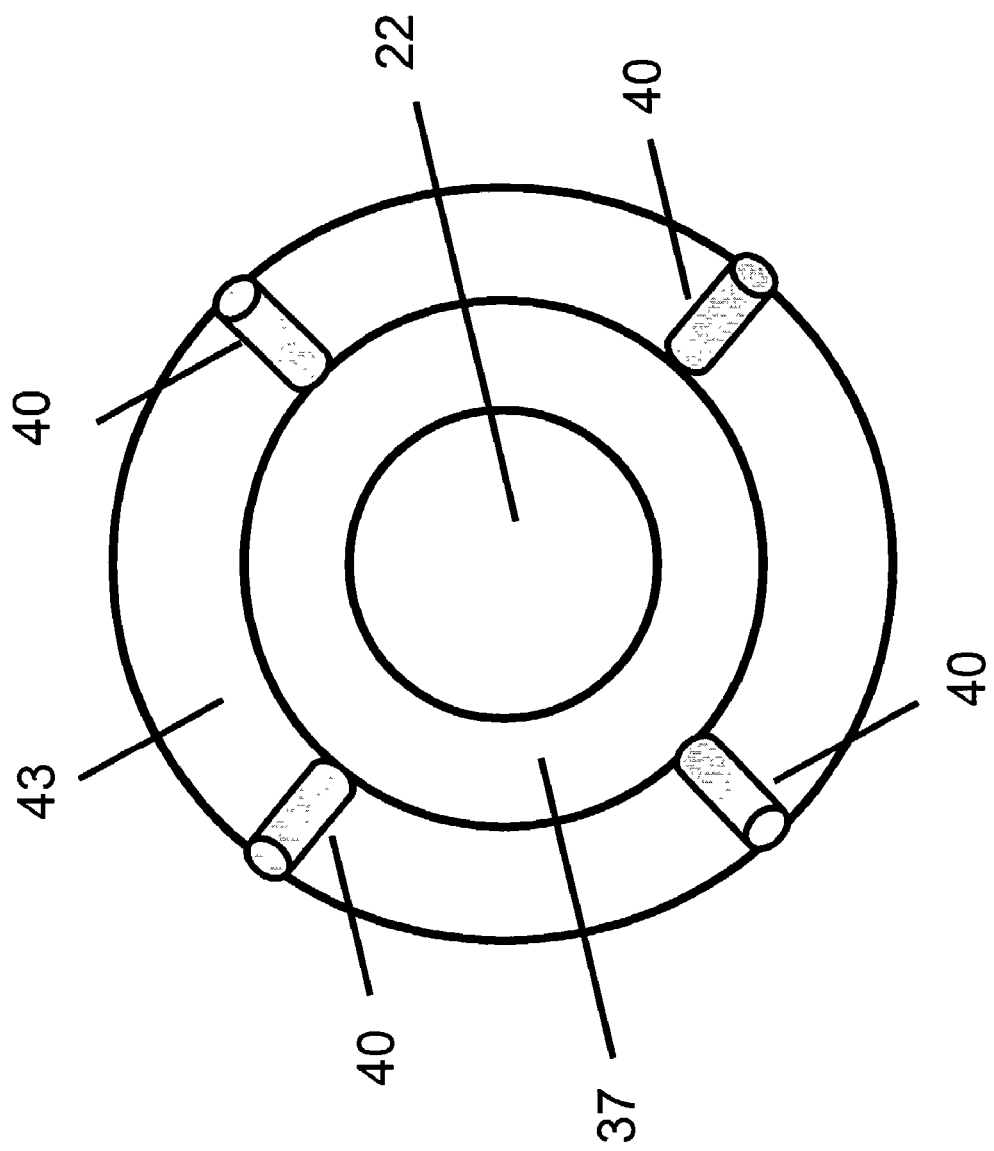
FIG. 5 is a cross-sectional view taken along line 5-5 of FIG. 2.
Figure 6:
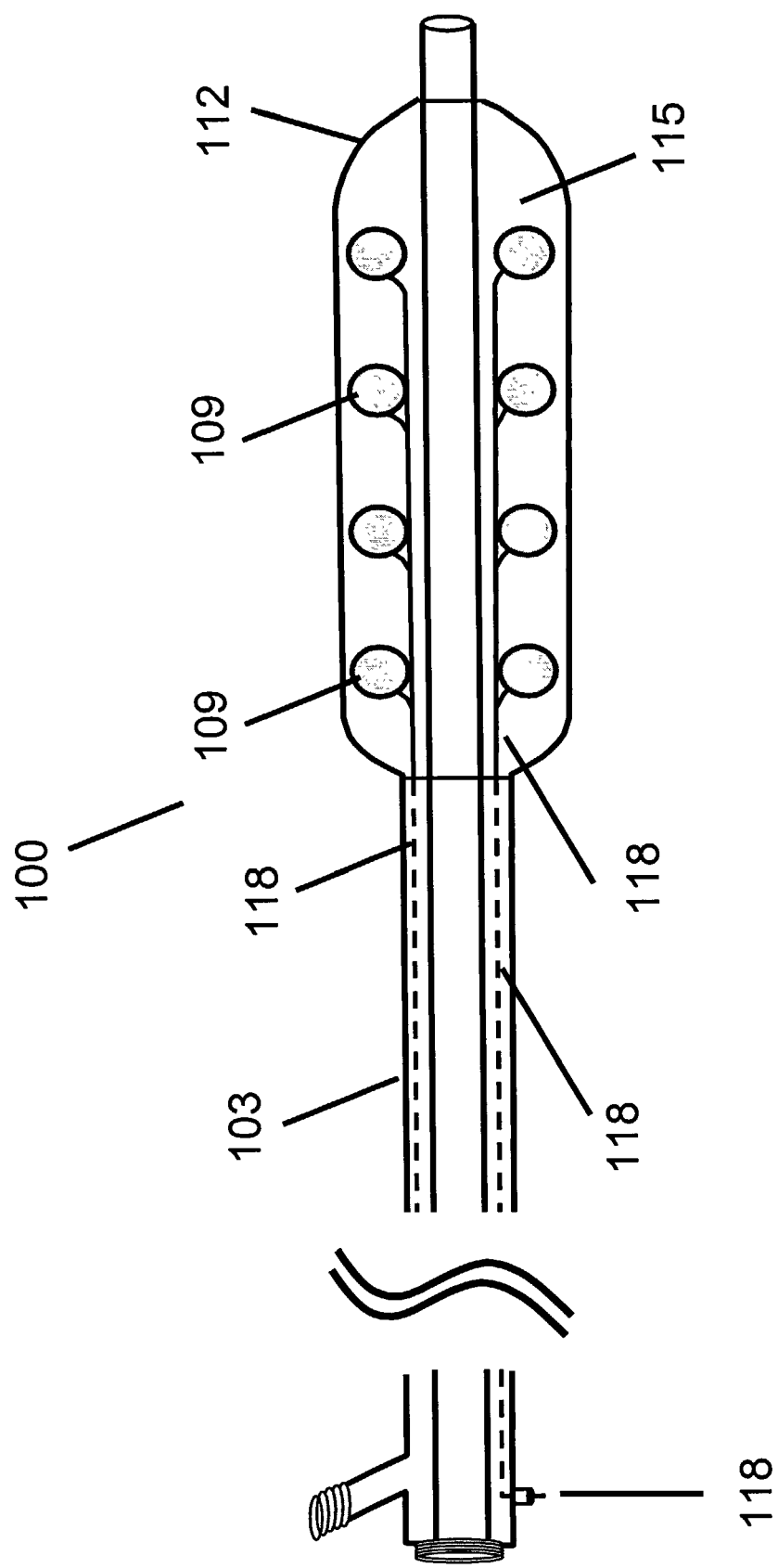
FIG. 6 is a side elevational view of an alternate embodiment of the present invention.
Figure 7:
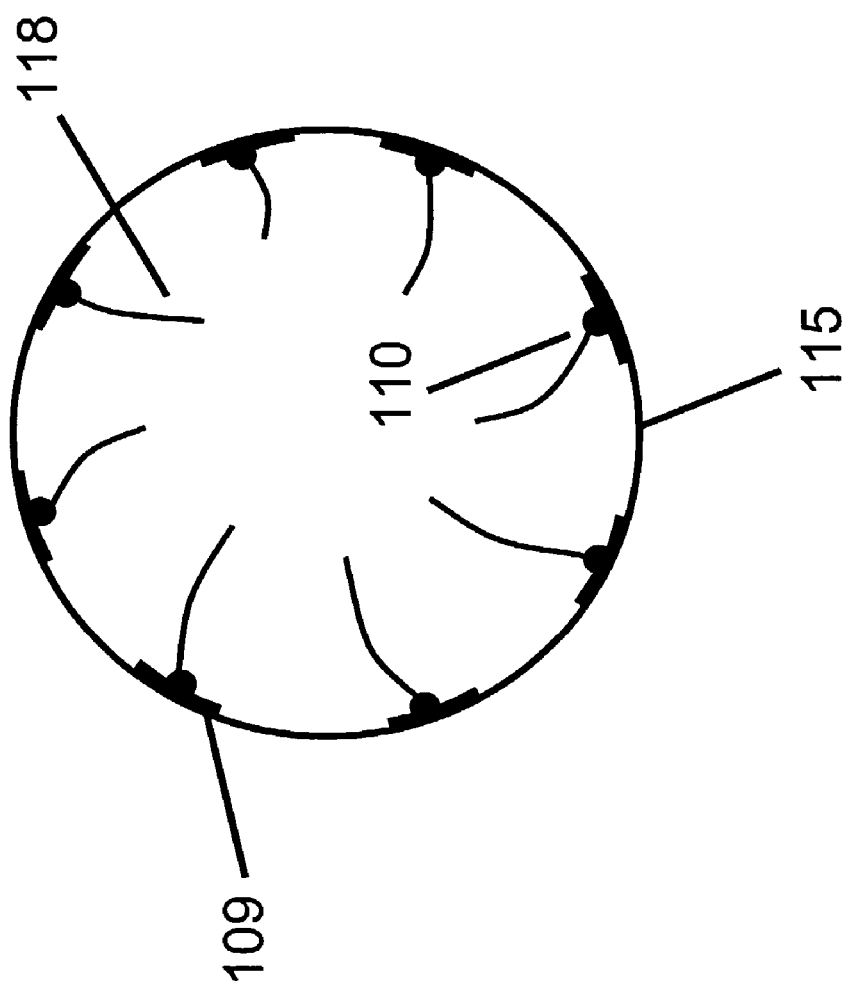
FIG. 7 is a cross-sectional view of the balloon catheter shown in FIG. 6.
Figure 8:
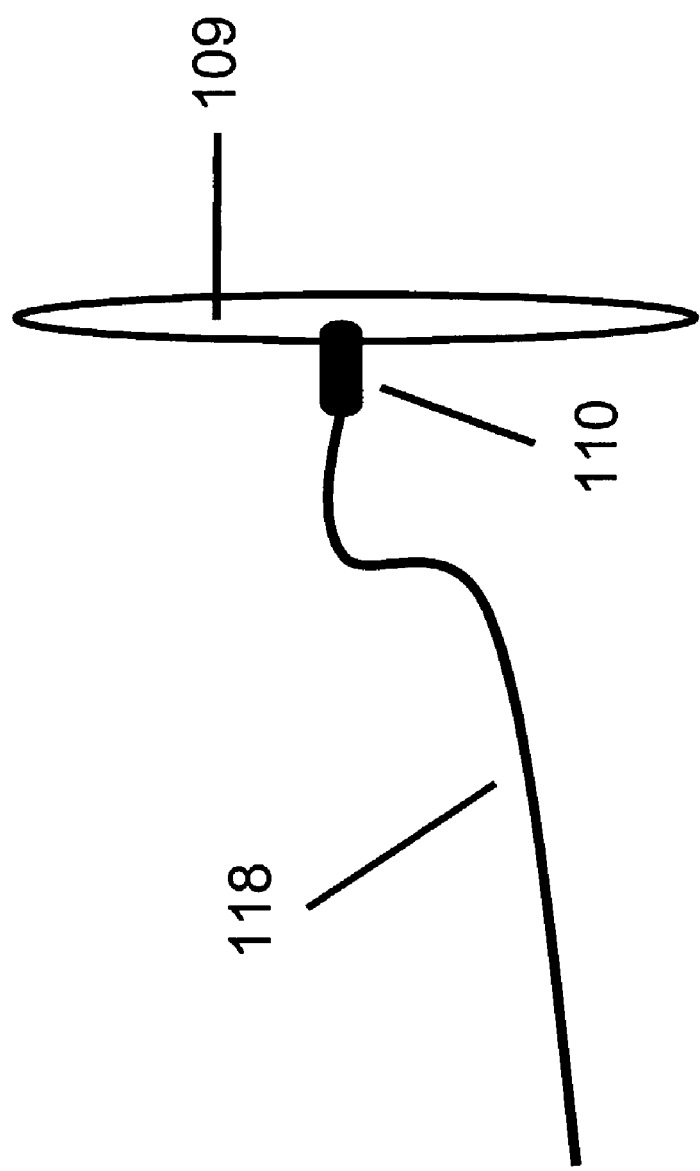
FIG. 8 is a perspective view of the string system of the balloon catheter of FIG. 6.
Figure 9:
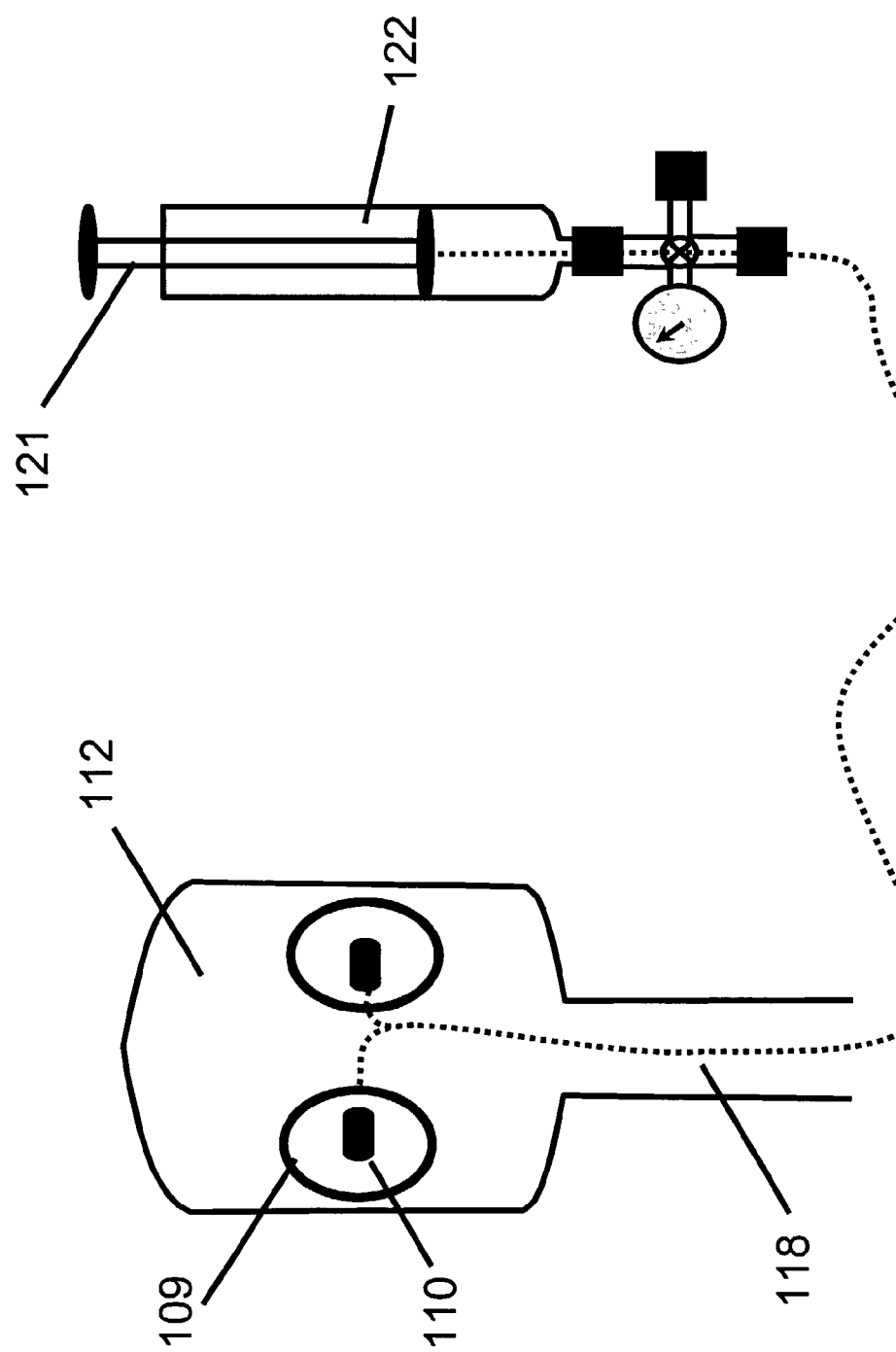
FIG. 9 is a schematic view of the string system and the syringe used with the balloon catheter of FIG. 6; and, FIG. 10 is a second alternate embodiment of the present invention.

In FIG. 5, the balloon 43 is shown in the inflated state.

In FIGS. 6-9 an alternate embodiment of the invention comprises a device 100 having a balloon catheter 103 having a suction mechanism for the removal of the plaque particles. The balloon catheter 103 includes flaps 109 of nylon or other appropriate biocompatible material. The flaps 109 are incorporated into the body 115 of the balloon 112. During inflation, the flaps 109 inflate with the body 115 of the balloon 112 while maintaining an airtight seal. A set of strings 118 connects to the inner wall of the flaps 109 by means of hooks 110 (FIGS. 7 and 8) and to the plunger 121 of the aspirating syringe 122 (FIG. 9) while passing through the lumen of the balloon catheter 103. During deflation, the strings 118 pull the flaps 109 back as the plunger 121 (FIG. 9) is pulled back to aspirate the contrast-saline mixture out of the balloon 112. The flaps 109 are disassociated from the body of the balloon 112 creating an inflow channel for debris into the lumen of the balloon catheter 103 and subsequently into the aspiration syringe 122. The disassociation of the flaps 109 precedes the deflation of the rest of the balloon 112 to prevent inadvertent release of trapped debris. The fluid will be withdrawn in addition to the free material released outside the balloon 112 from the vessel wall. The deflation of the balloon 112 because of its design with thinner walls or different material at its distal portion would be stepwise. The distal part of the balloon 112 would deflate last to avoid escape of debris particles distal to the site of angioplasty.

Figure 10:
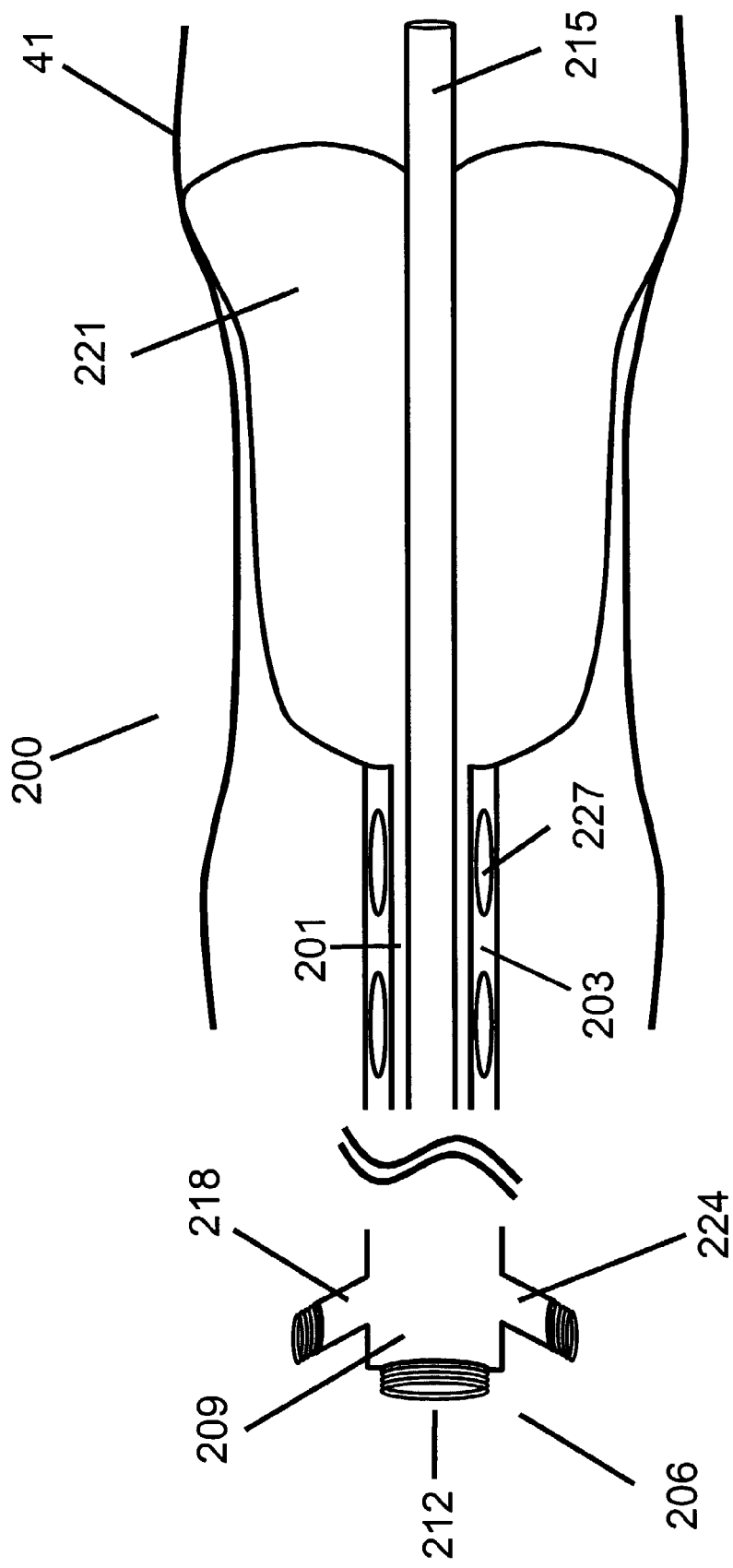

In FIG. 10, an alternate embodiment is shown. The device 200 comprises a balloon catheter 201 and a suction catheter 203 for the removal of the plaque particles. The device 200 includes three co-axial catheters. The proximal end 206 of the device 200 is connected to a three-way connector 209. The center port 212 of the connector 209 is coupled to the infusion catheter 215 (the inner most catheter). One of the side-branches 218 of the connector is connected to the balloon catheter 201 (the middle catheter) for inflating and deflating the balloon 221. The other side-branch 224 is connected to the suction catheter 203 (the outer most catheter). Upon the start of balloon deflating phase, a rapid suction of the debris is performed through at least one orifice 227 located on the suction catheter 203 proximal to the angioplasty balloon 221. The diameters of orifices 227 on the suction catheter 203 are adjusted to allow passage of large debris. The suction is performed using a standard syringe (not shown) connected to the corresponding port of the three-way connector 209. The balloon 221 itself is made of asymmetric material with the distal portion to be thinner that allows larger expansion of the balloon 221 at the distal segment. This larger expansion restrains the atherosclerotic particles within the balloon segment during deflation phase and ensures all of the particles to be suctioned out into the catheter and not travel with the blood stream. The deflation of the balloon 221 because of its design would be stepwise. The distal part of the balloon 221 would deflate last to avoid escape of debris particles distal to the site of angioplasty.

While the invention has been described in connection with certain embodiments, it is not intended to limit the scope of the invention to the particular forms set forth, but, on the contrary, it is intended to cover such alternatives, modifications, and equivalents as may be included within the spirit and scope of the invention as defined by the appended claims.

What is claimed is:

1. An angioplasty catheter, comprising:
   an infusion catheter having a proximal end and a distal end;
   a balloon catheter having an inflatable cavity formed by an inner wall and an outer wall, the balloon catheter having a proximal end and a distal end, the distal end of the balloon catheter sealingly attached to the infusion catheter, the balloon catheter having at least one communicating channel disposed from the outer wall to the inner wall of the balloon catheter; and,
   a suction catheter disposed between the balloon catheter and the infusion catheter, the suction catheter in fluid communication with the at least one communicating channel in the balloon catheter.

2. The angioplasty catheter of claim 1, wherein the infusion catheter, balloon catheter and suction catheter are all coaxial.

3. The angioplasty catheter of claim 1, wherein the suction catheter is integrally formed between an outer wall of the infusion catheter and the inner wall of the balloon catheter.

4. The angioplasty catheter of claim 1, wherein the balloon catheter has a plurality of communicating channels disposed along the length of the balloon catheter in the axial direction.

5. The angioplasty catheter of claim 1, wherein the distal end of the balloon catheter is capable of deflating at a slower rate than the proximal end of the balloon catheter such that during deflation the distal end of the balloon catheter remains engaged with an inner wall of a lumen for an initial period while the proximal end moves away from the inner wall of the lumen.

6. The angioplasty catheter of claim 1, wherein the wall thickness at the distal end of the balloon catheter is thinner than the wall thickness at the proximal end of the balloon catheter.

7. The angioplasty catheter of claim 1, wherein the distal end of the balloon catheter is constructed out of a different material than the proximal end.

8. An angioplasty catheter, comprising:
   an infusion catheter having a proximal end and a distal end;
   a balloon catheter having an inflatable cavity formed by an inner wall and an outer wall, the balloon catheter having a proximal end and a distal end, the distal end of the balloon catheter sealingly attached to the infusion catheter, the balloon catheter having at least one communicating channel disposed from the outer wall to the inner wall of the balloon catheter;

a suction catheter disposed between the balloon catheter and the infusion catheter, the suction catheter in fluid communication with the at least one communicating channel in the balloon catheter; and, wherein the material of the balloon catheter bordering the aperture has an accordion-like shape suitable for expansion when the balloon is inflated.

9. The angioplasty catheter of claim 1, wherein the material of the balloon catheter bordering the communicating channel is constructed out of a fibrous material.

10. An angioplasty catheter, comprising:

an infusion catheter having a proximal end and a distal end;

a balloon catheter disposed coaxially and surrounding the infusion catheter, the balloon catheter having a proximal end and a distal end, the distal end of the balloon catheter sealingly attached to the infusion catheter, the distal end of the balloon catheter capable of deflating at a slower rate than the proximal end of the balloon catheter such that during deflation the distal end of the balloon catheter remains engaged with an inner wall of a lumen during an initial period while the proximal end moves away from the inner wall of the lumen; and, a suction catheter disposed coaxially relative to the suction catheter and having a proximal end and a distal end, the distal end of the suction catheter sealingly attached to the balloon catheter, the suction catheter having at least one orifice disposed therein.

11. An angioplasty catheter for use in a lumen, the angioplasty catheter comprising:

an infusion catheter having a proximal end and a distal end;

a balloon catheter having an inflatable cavity formed by an inner wall and an outer wall, the balloon catheter having a proximal end and a distal end, the distal end of the balloon catheter sealingly attached to the infusion catheter, the balloon catheter having at least one communicating channel disposed from the outer wall to the inner wall of the balloon catheter; and, a suction catheter disposed between the balloon catheter and the infusion catheter, the suction catheter in fluid communication with the lumen through the at least one communicating channel in the balloon catheter.

* * * * *